United States Patent [19]

Battistini et al.

[11] Patent Number: 5,547,941

[45] Date of Patent: Aug. 20, 1996

[54] CYCLIC DINUCLEOTIDE DIPHOSPHOROTHIOATES, RELATED COMPOUNDS AND PHARMACEUTICAL COMPOSITIONS

[75] Inventors: Carlo Battistini, Novate Milanese; Silvia Fustinoni; Maria G. Brasca, both of Milan; Domenico Ungheri, Parabiago, all of Italy

[73] Assignee: Farmitalia Carlo Erba S.R.L., Milan, Italy

[21] Appl. No.: 354,888

[22] Filed: Dec. 9, 1994

Related U.S. Application Data

[63] Continuation of Ser. No. 914,923, Jul. 17, 1992, abandoned.

[30] Foreign Application Priority Data

Jul. 18, 1991 [GB] United Kingdom ............. 9115586

[51] Int. Cl.$^6$ .................. A61K 31/70; C07H 19/213; C07H 21/02; C07H 21/04
[52] U.S. Cl. .................. 514/44; 514/51; 536/26.11; 536/26.14; 536/26.2
[58] Field of Search ............. 536/26.11, 26.14, 536/26.20; 514/44, 51

[56] References Cited

PUBLICATIONS

Engelman et al., "HIV-1 DNA Integration: Mechanism of Viral DNA Cleavage and DNA Strand Transfer," *Cell*, 67, 1211–1221 (1991).

Hsu et al., "RNA Polymerase:, Linear Competitive Inhibition by Bis(3'→5')–cyclic Dinucleotides [c]NpNp," *Nucleic Acids Research*, 10(18), 5637–5647 (1982).

Falk et al., "Nucleoside und Nucleotide. Teil 3. Uber die Polykondensation von Thymidin–3'–phosphate Nach der Triestermethode," *Helv. Chim. Acta*, 55(6), 1928–1947 (1972).

Capobianco et al., "One Pot Solution Synthesis of Cyclic Oligodeoxyribonucleotides," *Nucleic Acids Res.*, 18(9), 2661–2669 (1990).

De Napoli et al., "Synthesis of Cyclic Branched Oligodeoxyribonucleotides," *Gazz. Chim. Ital.*, 121, 419–421 (1991).

Barbato et al., "Solid Phase Synthesis of Cyclic Oligodeoxyribonucleotides," *Tett. Lett.*, 28(46), 5727–5728 (1987).

Perno et al., "Different Pattern of Activity of Inhibitors of the Human Immunodeficiency Virus in Lymphocytes and Monocyte/Macrophage," *Antiviral Res.*, 17, 289–304 (1992).

Meltzer et al., "Macrophages as Susceptible Targets for HIV Infection, Persistent Viral Reservoirs in Tissue, and Key Immunoregulatory Cells that Control Levels of Virus Replication and Extent of Disease," *AIDS Res. Human Retroviruses*, 6(8), 967–971 (1990).

Battistini et al., "Synthesis of 3'–Fluoro–3'–deoxyadenosine Starting from Adenosine," *Synthesis*, 1990, 900–905.

Aerschot et al., "Synthesis and Antiviral Activity Evaluation of 3'– Fluoro–3'–deoxyribonucleosides: Broad Spectrum Antiviral Activity of 3'–Fluoro–3'–deoxyadenosine," *Antiviral Res.*, 12, 133–150 (1989).

*Genetic Engineering News*, Sep. 1, 1992, R. S. Root–Bernstein(II), "AIDS Is More Than HIV: Part I," pp. 4–6.

*Genetic Engineering News*, Sep. 15, 1992, R. S. Root–Bernstein(I), "AIDS Is More Than HIV: Part II," pp. 4–5.

*Scientific American*, vol. 270, No. 1, issued 1994, Beardsley, "Trends in Cancer Epidemiology. A War Not Won," pp. 130–138.

Battistini et al., "Stereoselective Synthesis of Cyclic Dinucleotide Phosphorothioates," Abstract of presentation to *Fine Organic Chemistry Colliquium*, ERAI(sponsor), Orangerie, France, October 21–23, 1992, p. 17.

Battistini et al., "Stereoselective Synthesis of Cyclic Dinucleotide Phosphorothioates," *Tetrahedron*, 49(5), 1115–1132 (1993).

*Primary Examiner*—John Knight, III
*Assistant Examiner*—L. Eric Crane
*Attorney, Agent, or Firm*—Oblon, Spivak, McClelland, Maier, & Neustadt, P.C.

[57] ABSTRACT

There are provided compounds of formula (I)

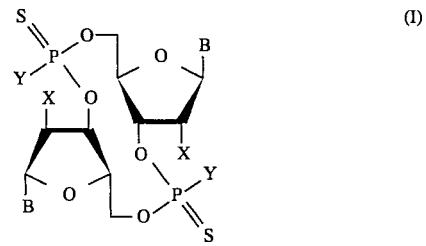

wherein
  each group B is, independently, a naturally occurring or modified heterocyclic base linked through a nitrogen or a carbon atom of the ring to the sugar moiety;
  each group X is a, independently, hydrogen, fluorine, hydroxy, or a $C_1$–$C_6$ alkoxy group;
  each group Y is, independently, hydrogen, sulphidryl or hydroxy; and the pharmaceutically acceptable salts thereof.

A process for their preparation and pharmaceutical compositions comprising them are also described. The compounds of this invention can be useful as antivirals, particularly as anti–HIV (Human Immunodeficiency Virus) agents, namely as drugs to be used against AIDS (Acquired Immunodeficiency Syndrome) therapeutically and/or prophylatically.

6 Claims, No Drawings

CYCLIC DINUCLEOTIDE DIPHOSPHOROTHIOATES, RELATED COMPOUNDS AND PHARMACEUTICAL COMPOSITIONS

This application is a continuation of application Ser. No. 07/914,923, filed on Jul. 17, 1992, now abandoned.

The present invention relates to cyclic oligonucleotides phosphorothioates, to a process for their preparation and to pharmaceutical compositions comprising them.

The compounds of this invention can be useful as antivirals, therapeutically and/or prophylatically.

The present invention provides a compound of the formula (I)

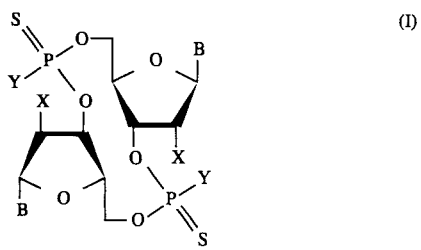

wherein each group B is, independently, a naturally occurring or a modified heterocyclic base linked through nitrogen or a carbon atom of the ring to the sugar moiety;

each group X is, independently, hydrogen, fluorine, hydroxy or a $C_1$–$C_6$ alkoxy group; and each group Y is, independently, hydrogen, sulphidryl or hydroxy group.

This invention includes also the pharmaceutically acceptable salts of the compounds of formula (I) as well as the possible diastereomers covered by formula (I), both separately and in mixture.

Preferably, when B is a naturally occurring heterocyclic base it is, e.g., cytosine, thymine, uracil, guanine, adenine or hypoxanthine, more preferably cytosine or thymine.

Preferably, when B is a modified heterocyclic base, it is, e.g., diaminopurine or 8-bromoadenine. When X is a $C_1$–$C_{C6}$ alkoxy group it is, preferably, a methoxy group.

More preferably X is hydrogen or a hydroxy group.

Preferably Y is a hydroxy or a sulphidryl group.

In the compounds of formula (I) when Y is a hydroxy group it is intended that the structure

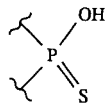

is equivalent to

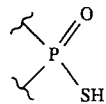

and the structures

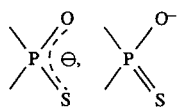

and

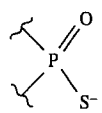

are equivalent to each other

It is also intended that, in the compounds of formula (I), the configuration at the phosphorus atoms may independently be R ($R_P$ configuration) or S (Sp configuration); both pure diastereomers and mixtures of diastereomers are encompassed by the present invention. In the present specification the term diastereomers means compounds differing only for the configuration of one or more of their chiral centers (stereoisomers) but that are not enantiomers (not superimposable mirror images). As already said, the invention includes also the pharmaceutically acceptable salts of the compounds of formula (I).

The salts include salts with pharmaceutically acceptable bases, both inorganic bases such as, for instance, alkali metal e.g. sodium or potassium, hydroxides or ammonia, and organic bases such as, for instance alkylamines, e.g. methylamine or triethylamine, aralkylamines, e.g. benzylamine, dibenzylamine, α or β-phenylethylamine, or heterocyclic amines such as, e.g., piperidine, 1 methyl piperidine, piperazine or morpholine.

Examples of specific compounds preferred under this invention are the following compounds, both as pure $R_PR_P$ or $S_PR_P$ diastereomers and as diastereomeric mixture of $R_PR_P$ and $S_PR_P$ diastereomers:

cyclo-2'-deoxy-P-thiocytidylyl-(3'→5')-2'-deoxy-P-thio-cytidylyl-(3'→5'), cyclo-2'-deoxy-P-thiothymidylyl-(3'→5')-2'-deoxy-P-thiothymidylyl-(3'→5'), and the pharmaceutically acceptable salts thereof.

A preferred salt, according to the invention cyclo-2'-deoxy-P-thiocytidylyl-(3→5')-2'-deoxy-thiocytidylyl-(3'→5') disodium salt of formula (II)

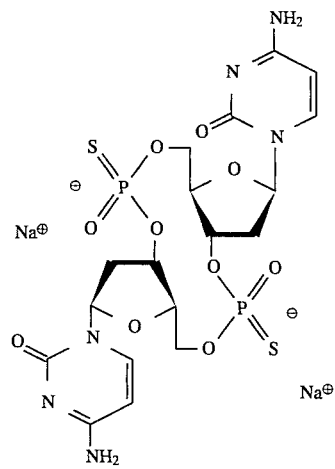

(II)   $R_p,R_p + S_p,R_p$ diastereomeric mixture
(IIa)  $R_p,R_p$ diastereomer
(IIb)  $S_p,R_p$ diastereomer The compounds of the present invention can be prepared by a process comprising A) reacting a compound of formula (ii)

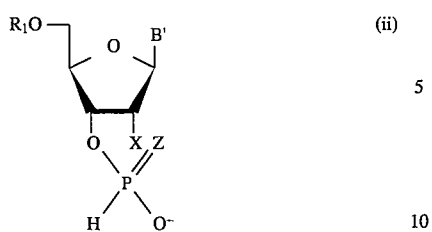

wherein
R₁ is a hydroxy protecting group, B' is a group B as defined above wherein, if present, one or more exocyclic amino groups of the heterocyclic base are protected by an amino protecting group, Z is oxygen or sulphur and X is as defined above, provided that, when X is a hydroxy group, it is properly protected by a suitable hydroxy protecting group, with a compound of formula (iii)

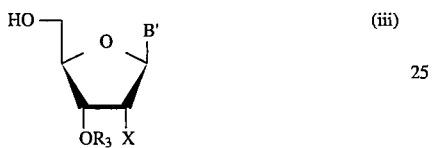

wherein R₃ is a hydroxy protecting group cleavable differently from R₁,
B' and X are as defined above;

B) optionally thiooxidizing or oxidizing a resultant compound of formula (iv)

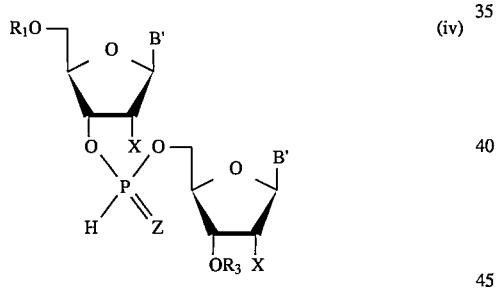

wherein R₁, B', Z, X and R₃ are as defined above with a thiooxidizing or an oxidizing agent;

C) optionally separating the resultant diastereomeric mixture of a compound of formula (v) into the single diasteromers;

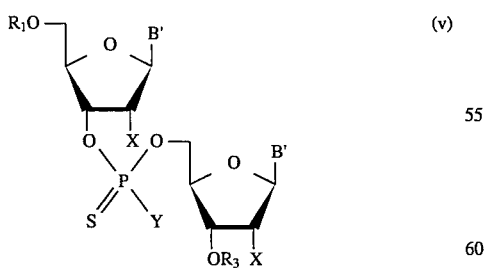

wherein R₁, R₃, B', Y and X are as defined above into the single diasteromers;

D) removing the protecting group R₃ from a compound of the above formula (v) to obtain a compound of formula (vi)

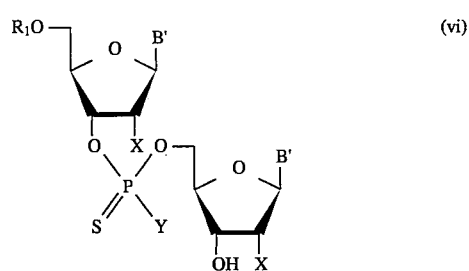

wherein
R₁, B' X and Y are as defined above;

E) phosphorylating or thiophosphorylating the free hydroxy group in 3'position of the compound of the above formula (vi), to obtain a compound of formula (vii)

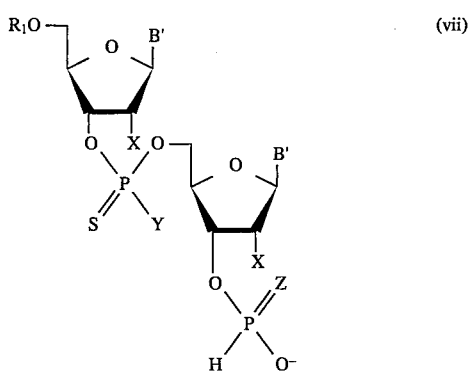

wherein
R₁, B' X Y and Z, are as defined above;

F) removing the group R₁ from a compound of the above formula (vii), to obtain a compound of formula (viii)

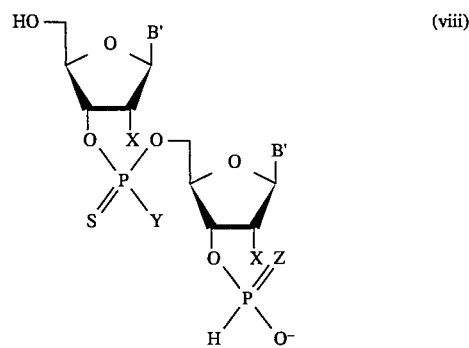

wherein B' X Y and Z are as defined above;

G) cyclizing a compound of formula (viii) to obtain a compound of formula (ix)

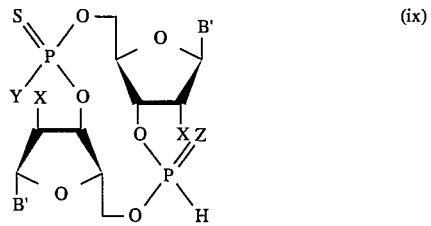

wherein B', X, Y and Z are as defined above;

H) optionally thiooxidizing or oxidizing a compound of the above formula (ix) with a thiooxidizing or an oxidizing agent and, if necessary, removing the protecting groups still possibly present on a compound of formula (ix), to obtain the desired compound of formula (I) and, if desired, separating the diastereomeric mixture of a compound of formula (I) into single diasteromers and/or, if desired, salifying a compound of formula (i) or obtaining a free compound from a salt.

In the above formulae, when B' is a group B, wherein one or more exocyclic amino groups are present on the heterocyclic base, said amino groups may be protected by a suitable amino protecting group such as, e.g., benzoyl or isobutyryl.

In the compound of formula (ii) and (iii) the hydroxy protecting groups may be, e.g., dimethoxytrityl, monomethoxytrityl, pixyl, terbutyldimethylsilyl, terbutyldiphenylsilyl, p-nitrophenylethylcarbonyl, p-chlorophenylsulphonylethoxycarbonyl, fluorenylmethyloxy carbonyl or 4-methoxytetrahydropyran-4-yl.

The reaction between a compound of formula (ii) and a compound of formula (iii) and the intramolecular cyclization of a compound of formula (viii) may be carried out in an organic solvent such as, e.g., pyridine, pyridine-acetonitrile or triethylamine-acetonitrile, in the presence of a condensing agent such as, e.g., a hindered acyl halide, arylsulphonylchloride or diarylchlorophosphate, preferably in the presence of pivaloyl chloride or adamantoyl chloride.

The optional thiooxidation of a compound of formula (iv) in step B), or of a compound of formula (ix) in step H) may be performed with known thiooxidizing agents such as, e.g., elemental sulphur ($S_6$); preferably with a suspension of sulphur in pyridine, a solution of sulphur in carbon disulphide, 3H-1,2-benzodithiole-3-one-1,1-dioxide in triethylamine acetonitrile, aroyl disulfide or arylacyldisulfide in dichloroethane with an organic base, or tetraethylthiuram disulfide in acetonitrile.

The optional oxidation of a compound of formula (iv) in step B) or of a compound of formula (ix) in step H) may be carried out in a conventional manner of the nucleotide chemistry, for example with iodine in an appropriate solvent, such as, e.g., pyridine-water.

The optional separation of the diastereomeric mixture of a compound of formula (v) in step C) may be carried out using known methods currently used in the chemistry such as, e.g., silica gel column chromatography.

As from step D) the synthetic pathway may be carried out either with the diastereomeric mixture or with each single diastereomer.

The deprotection of the protected hydroxy groups, possibly present on the compounds involved in the process, may be usually carried out with a suitable deprotecting agent such as, e.g., tetrabutylammonium or cesium fluoride, when silyl groups are used as protecting agents; or bases like DBU (1,8-diazabicyclo [5.4.0]-undec-7-ene) or thrietylamine, when paranitrophenylethyloxycarbonyl, p-chlorophenylsulphonylethyloxycarbonyl, fluorenylethyloxycarbonyl groups are used as protecting agents; or inorganic or organic acids like benzene sulphonic acid or zinc bromide in aprotic solvent, e.g. methylene chloride, when trityl groups, e.g. dimethoxy trityl or pixyl groups, are used as protecting agents.

The free hydroxy group of a compound of formula (vi) may be phosphorylated by using a suitable phosphorylating agent, such as, e.g., phosphorus trichloride, phosphorus tristriazolide and N-methylmorpholine in dry dipolar aprotic solvent.

The free hydroxy group of a compound of formula (VI) may be thiophosporylated by using triethylammonium phosphinate and pivaloyl chloride in pyridine and successive thiooxidation with sulphur to the corresponding H-phosphonothioate or by using phosphorus tristriazolide and successive treatment with hydrogen sulphide and N-methylmorpholine to give the corresponding hydrogenphosphonodithioate that can be cyclized in step G by using N-methyl-2-chloropyridinium iodide.

The deprotection of the amino protecting groups possibly present on the heterocyclic base, may be carried out, after the intramolecular cyclization with a suitable amino deprotecting agent such as, e.g., ammonia in water-dioxane, ethylenediamine in ethanol, or aqueous hydrazine in pyridine-acetic acid.

The compounds of formula (ii) and (iii) are known compounds and may be prepared following known procedures.

For example the compounds of formula (ii) may be prepared according to the method described in "B.C. Froehler et al, Nucleic Acid Research 14, 5399,(1986)" and the compounds of formula (iii) may be prepared according to the method described in "K. Ogilvie, Nucleosides Nucleotides and their Biological Application, (1983), Academic Press, p.2091".

Alternatively, the condensation of step A), the phosphorylation of step E) and the cyclization of step G) may be carried out by using analogous methodologies well established in the art such as, for example, hydroxy-benzotriazole and phosphoramidite method.

A preferred example of realization of this process is outlined in the following scheme I showing the preparation of the compound like the one represented in formula II, starting from a commercially available nucleoside like III.

In more detail, a 5'-O-protected nucleoside optionally protected also at the exocyclic amino group of the heterocyclic moiety like III, for example $N^4$-benzoyl-5'-O-dimethoxytrityl-2'deoxycytidine, is made to react with a P (III) phosphorous triazolide or better with the product obtained by mixing phosphorous trichloride, triazole and N-methylmorpholine in dry dichloromethane or in other dry dipolar aprotic solvent, according to a known procedure [B. C. Froehler et al., Nucleic Acid Research 14, 5399 (1986)], to give a nucleotid-3'-hydrogenphosphonate like IV. A properly protected nucleoside having a free 5'-hydroxy group like VI can be obtained by the same starting compound III through protection of the 3'position and deprotection of the 5'position. As example, a 5'-O-dimethoxytrithyl (DMT) derivative (V; $R^1$=DMT, $R^2$=benzoyl, $R^3$=—Si(CH$_3$)$_2$C(CH$_3$)$_3$ can be prepared and, selectively deprotected at the 5'position by acidic treatment, according to known procedures: [K. Ogilvie, Nucleosides and their Biological Application, 1983, Academic Press, p. 209], to give a protected nucleoside like VI.

The hydrogenphosphonate-nucleotide of the type IV and the nucleoside type VI can be coupled in a dry solvent like pyridine by adding a condensing agent, for example a hindered acyl halide, preferably pivaloyl chloride or adamantoyl chloride. This coupling procedure has to be followed by an oxidation stage performed with elemental sulphur ($S_a$) or better a suspension of sulphur in pyridine or a solution of sulphur in carbon disulphide, or other known thiooxidizing agents like 3H-1,2-benzo-dithiole-3-one-1,1-dioxide or an aroyl disulfide or an arylacyldisulfide or tetraethylthiouram difulside.

This process gives a high yield of a protected (3'→5')phosphorothioate-dinucleotide like VII as a mixture of diastereomers differing for the phosphorus configuration ($R_P$ or $S_P$) with a prevalence of the $S_P$ configuration (for example $S_P$:$R_P$=65:35, when in VII $R^1$=DMT, $R^2$=benzoyl, $R^3=Si(CH_3)_2C(CH_3)_3$). The two diastereomers can be separated by silica gel column chromatography and the configuration at the phosphorus atom can be assigned by criteria based on analogy of analytical data (for example $^{31}$P NMR and HPLC) with other data on the literature and by the different sensitivity of the corresponding fully deprotected analogs to the hydrolytic action of enzymes. The synthetic pathway to the cyclic oligonucleotide of the type may be independently performed starting from the $S_{P\text{-}VII\text{ or }RP}$-VII diastereomer.

A dinucleotide like VII as a single diastereomer is selectively deprotected at the 3'position (for example with tetrabutylammonium fluoride if $R^3=Si(CH_3)_2C(CH_3)_3$) to give an intermediate like VIII. The 3'-hydroxyl group of VIII can be phosphorylated by treatment with a P (III) phosphorylating agent, like phosphorus trichloride, or phosphorus triazolide, or better with the product obtained by mixing phosphorus trichloride, triazole and N-methylmorpholine in dry dichloromethane or in other dry dipolar aprotic solvent to give a 3'-O-hydrogenphosphonate derivative of the type IX. At this point of the synthetic process the 5'position of the dinucleotide can be deblocked by a proper treatment, (for example, an acidic treatment with zinc bromide or benzenesulfonic acid in aprotic solvent, preferably, at low temperature if the protecting group $R^1$ is a dimethoxytrityl group), to afford an intermediate like X. The key step of our synthetic process is the intramolecular condensation to give a cyclic backbone that is a new process for a new type of structure. It is performed by adding a condensing agent, for example, a hindered acyl halide, preferably pivaloyl chloride or adamantoyl chloride, to a solution of the dinucleotide X having a concentration in a dry polar aprotic solvent like a mixture of pyridine and dimethylformamide, better if under nitrogen atmosphere and at room temperature, leaving the mixture to react for the necessary period of time, preferably from 30 to 60 minutes. In our examples as a successive step, elemental sulphur ($S_a$), or better a suspension of sulphur in pyridine, or a solution of sulphur in carbon disulphide, or other known thiooxidizing agent, is added to obtain a cyclic oligonucleotide phosphorothioate like XI. In the case of protection of the exocyclic aminogroup at the heterocyclic base as exemplified in the scheme, a treatment (like ammonia in water-dioxane if $R^2$ is a benzoyl group) provides the last deprotection, to give the final compound having a structure type II. Noteworthy the intramolecular internucleotidic condensation shows to be completely stereoselective for $R_P$ configuration, namely the second chiral phosphorus atom introduced occurs to have only $R_P$ configuration whatever is the configuration of the other phosphorus atom firstly introduced.

SCHEME 1

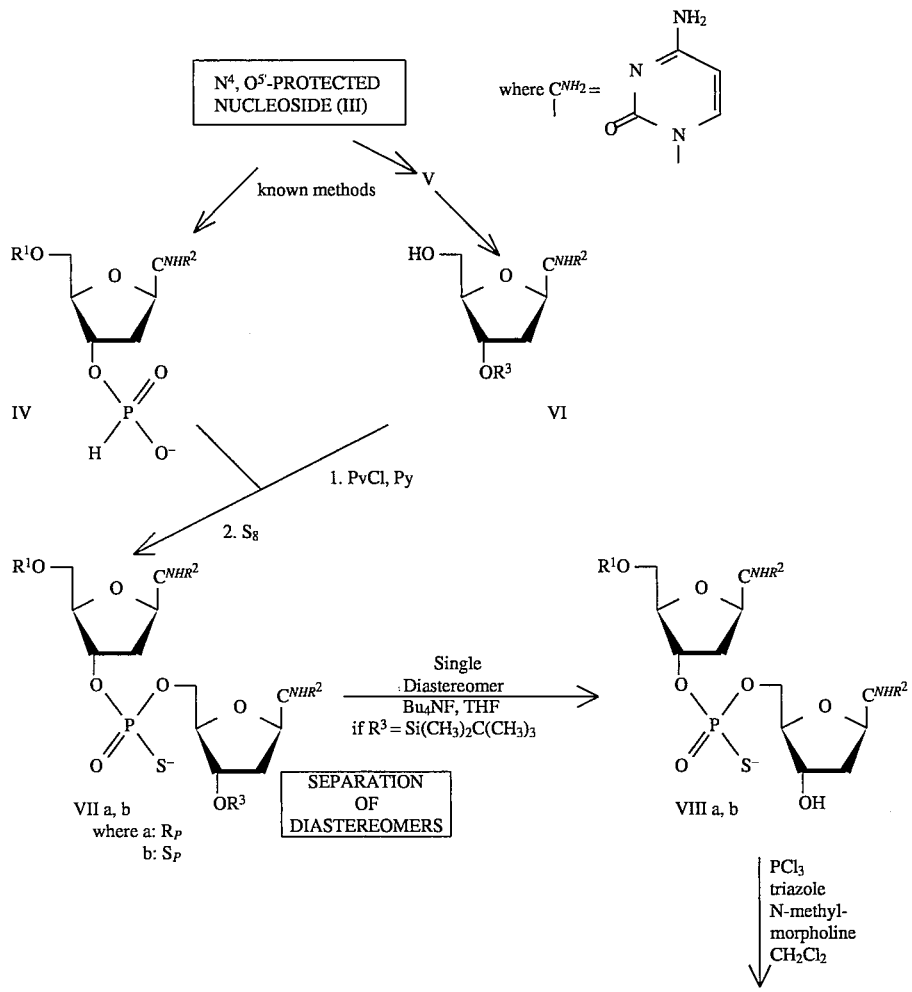

-continued
SCHEME 1

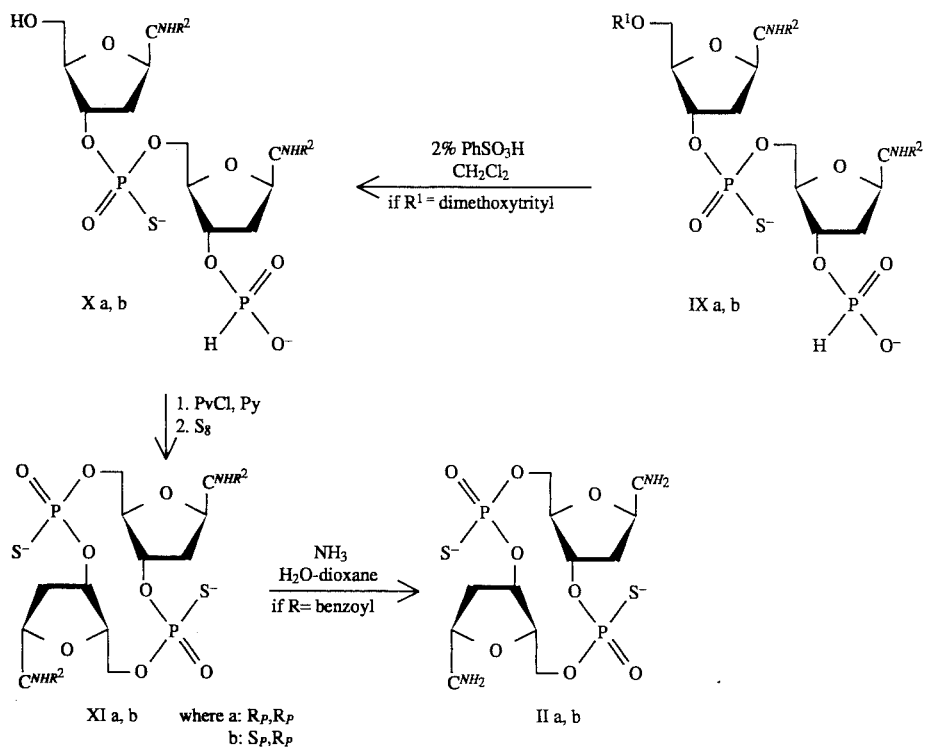

As mentioned above, the configuration at the phosphorus atom of the phosphorothioate internucleotide moiety, firstly introduced along the synthetic pathway, can be determined by evaluating the rate of enzymatic degradation of the completely deprotected analogs of the separated diastereomers of the synthetic intermediate, namely VIIa and VIIb, obtained in a ratio 35:65 respectively in the case described as representative example. The two diastereomers are independently deprotected at the position 3'in the synthetic process affording respectively the intermediates VIIIa and VIIIb. Moreover the last two diastereomers can be independently further deprotected apart from the synthetic process and for analytical purpose giving XIIa and XIIb as final samples according to scheme 2:

SCHEME 2

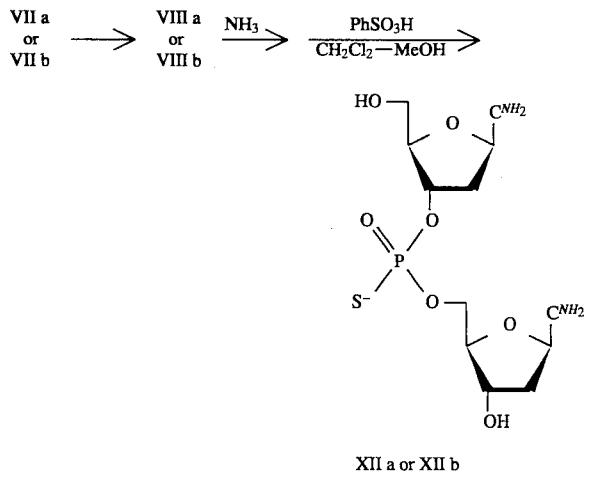

The two samples XIIa and XIIb can independently undergo an enzymatic degradation by action of an exonuclease like snake venom phosphodiesterase following the disappearance of starting sample by HPLC along the time. In the present example the sample XIIa was degraded much faster than the sample XIIb. Accordingly the configuration $R_P$ has to be assigned to XIIa and configuration $S_P$ to XIIb.

So the process to oligodeoxyribonucleotide phosphorothioate involving H-phosphonate method and thio-oxidation happens to be stereoselective in a certain degree in favour of $S_P$ configuration, that is $S_P$:$R_P$ 65:35.

Anyway, much more striking and unexpected is the result of the stereochemical elucidation of the phosphorothioate moiety formed in the cyclization step, namely the second chiral phosphorus introduced along the synthetic pathway The assignment of configuration at this phosphorus atom has been deduced from the fact that both the open dinucleotide $R_P$ (Xa) and the diastereomer $S_P$ (X b) after cyclization to XI give only one of the two possible diastereomers and the product of the reaction is different in the two cases. Indeed XIa and hence IIa can be the $R_P$,$R_P$-diastereomer or the $R_P$,$S_P$-diastereomer, on the other hand XIb and hence IIb can be $S_P$,$R_P$-diastereomer (that is identical the $R_P$,S-diastereomer) or $S_P$,$S_P$-diastereomer.

The $^{31}P$ NMR spectrum of IIa shows only one signal that is the case of the $R_P$,$R_P$-diastereomer, on the contrary the $^{31}P$ NMR spectrum of IIb shows two signals of equal intensity indicating unequivocally that IIb is the $S_P$, $R_P$-diastereomer.

In conclusion, either starting from the $R_P$ uncyclized dinucleotide Xa or the $S_P$ analog Xb, the cyclization step followed by thiooxidation is characterized by a complete $R_P$-stereoselectivity.

The phosphorothioate formation by the methodology shown in scheme 1 involves two steps: the internucleosidic coupling to an H-phosphonate derivative and a subsequent thiooxidation. It has been recently proved [F. Seela, "9$^{th}$ International Round Table- Nucleosides, Nucleotides & their Biological Applications", Jul. 30–Aug. 3, 1990, Uppsala (Sweden)]that the thiooxidation of separated H-phosphonate diastereomers is a "stereospecific" process. This finding leads to the conclusion that, in both the cases of asymmetric induction occurring in our process, the stereoselectivity actually takes place at the level of the first new chiral center formation. namely at the level of the H-phosphonate diester formation. This means that the herein described processes are also "stereoselective" processes for the formation of linear oligodeoxyribonucleotides H-phosphonate and cyclic oligodeoxyribonucleotides H-phosphonate.

The compounds of the present invention were tested for antiviral activity on peripheral human lymphocytes isolated by density gradient centrifugation and stimulated with a mitogen.

Infection was performed with a standardized preparation of HIV and cells, cultured in the presence of the drug for 4 days.

Individual cultures were established to measure viral replication 2, 3 and 4 days after infection. The amount of viral core protein P 24, synthesized and released by the infected cells, was determined in the supernatant of treated and untreated cells on days 2, 3 and 4 by an Elisa.

The total amount of viral RNA synthesized by the infected lymphocytes was determined on day 2, 3 and 4 by a nucleic acid hybridization technique. By including a standard preparation of HIV-RNA, the amount of synthesized RNA was quantified.

The antiviral effect induced by the tested compounds was calculated from the inhibition of the evaluated parameters (i.e.: P24 or RNA) as compared with infected controls.

The anti-HIV activities of representative compounds of the present invention are reported in tables 1 and 2.

TABLE 1

Anti-HIV activity of compound IIb

|  |  | Day 2 | Day 3 | Day 4 |
|---|---|---|---|---|
| Inhibition of HIV replication on the protein level | | | | |
| Compound IIb (10 μM) | (ng p24/ml) | 0.0 | 0.0 | 3.7 |
| Control | (ng p24/ml) | 0.0 | 2.2 | 21.5 |
| Inhibition | (%) |  | 100 | 83 |
| Inhibition of HIV replication on the RNA level | | | | |
| Compound IIb (10 μM) | (pg RNA/ml) | 0 | 0 | 266 |
| Control | (pg RNA/ml) | 0 | 226 | 612 |
| Inhibition | (%) |  | 100 | 56 |

TABLE 2

Anti-HIV activity of compound IIa

|  |  | Day 2 | Day 3 | Day 4 |
|---|---|---|---|---|
| Inhibition of HIV replication on the protein level | | | | |
| Compound IIa (10 μM) | (ng p24/ml) | 0.0 | 0.1 | 17.1 |
| Control | (ng p24/ml) | 0.0 | 2.2 | 21.5 |
| Inhibition | (%) |  | 97 | 20 |
| Inhibition of HIV replication on the RNA level | | | | |
| Compound IIa (10 μM) | (pg RNA/ml) | 0 | 188 | 465 |
| Control | (pg RNA/ml) | 0 | 226 | 612 |
| Inhibition | (%) |  | 17 | 24 |

Compound IIa represents the $R_P R_P$ diastereomer of the compound of formula (II) (our internal code FCE 26660A). Compound IIb represents the $S_P R_P$ diastereomer of the compound of formula (II) (our internal code FCE 26661A). As shown in the above table 1, at the non cytotoxic concentration of 10 μM the compound IIb was able to inhibit the HIV p24 expression by 100% at the third day and by 83% at the fourth day and it was able to reduce the HIV RNA level of 100% at the third day and of 56% at the fourth day after the compound administration. The compounds of the invention can be administered in a variety of dosage forms, e.g., orally in the form of tablets, capsules, sugar or film coated tablets, liquid solutions or suspensions; rectally, in the form of suppositories; parenterally, e.g. intramuscularly, or by intravenous injection or infusion, or topically.

The dosage depends on the age, weight, conditions of the patient and administration route; for example the dosage adopted for i.v. administration to adult humans may range from about 10 to about 500 mg per dose, from 1 to 4 times daily.

The invention includes pharmaceutical compositions comprising a compound of the invention as active principle in association with a pharmaceutically acceptable excipient (which can be a carrier or diluent). The pharmaceutical compositions containing the compounds of the invention are usually prepared following conventional methods and are administered in a pharmaceutically suitable form.

For example, the solid oral forms may contain, together with the active compound, diluent, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulpathes; and, in general, non-toxic and pharmacologically inactive substances used in pharmaceutical formulations. Said pharmaceutical preparations may be manufactures in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. Compositions for topical application such as, e.g. creams, lotions or pastes, may be, e.g. prepared by admixing the active ingredient, with a conventional oleaginous or emulsifying excipient.

The following examples illustrate the invention without limiting it. In these examples NMR data are given indicating with A the 5' end nucleoside (the left top one of the structures as drawn in the schemes) and with B the 3' end nucleoside (the right bottom one of the structures as drawn in the schemes).

EXAMPLE

Example 1

$R_P$ and $S_P$ $N^4$-benzoyl-5'-O-(dimethoxytrityl)-2'-deoxy-p-thiocytidylyl-(3'→5')-$N^4$-benzoyl-3'-O-(t.butyldimethyllsilyl)-2'-deoxycytidine, triethylammonium salt (VIIa and VIIb with $R^1$=DMT, $R^2$=Bz, $R^3$=TBDMS) $N^4$-Benzoyl-5'-O-(dimethoxytrityl)-2'-deoxycytidine-3-(hydrogenphosphonate), triethylammonium salt (IV) (8.8 g, 11.0 mmol) and $N^4$-benzoyl-3'-O-(t.butyldimethylsilyl)-2'-deoxycytidine (VI) (4.9 g, 11.0 mmol) were dried by coevaporation with dry pyridine and dissolved in the same solvent (120 ml). Distilled pivaloyl chloride (3.39 ml, 27.5 mmol) was added dropwise and the reaction mixture was stirred under nitrogen atmosphere for 30 minutes at room temperature. Elemental sulphur (3.52 g, 110 mmol) was added and, after 3 hours, the reaction was quenched by addition of triethylamine (10 ml). The reaction mixture was concentrated under vacuum, the residue dissolved in dichloromethane, washed with water, dried ($Na_2SO_4$) and evaporated under vacuum. Purification and separation of the diastereomers $R_P$ and $S_P$ was accomplished by two silica gel column chromatographies using a linear gradient from ethyl acetate to ethyl acetate/methanol 95:5. The two products were obtained with a total yield of 70%.

The higher $R_f$ compound was the $R_P$ isomer (VIIa) (3.87 g, 28% yield). TLC on silica gel: $R_f$ 0.34 eluting with ethyl acetate/methanol 85:15. $^1$H NMR (400 MHz, DMSO-$d_6$): δ=0.07 (s, 6H, 2 Si$CH_3$); 0.66 (s, 9H, SiC($CH_3$)$_3$); 2.1–2.6 (m, 4H, $CH_2$2'A+$CH_2$2'B); 3.2–3.4 (m, 2H, $CH_2$5'A); 3.72 (s, 6H, 2 $CH_3$); 3.7–4.1 (m, 3H, H4'B+$CH_2$5'B); 4.32 (m, 1H, H4'A); 4.50 (m, 1H, H3'B); 5.06 (m, 1H, H3'A); 6.15, 6.18 (two dd, J=6.3 Hz, 2H, H1'A+H1'B); 6.87 (d, J=8.5 Hz, 4H, aromatic H's ortho to $OCH_3$); 7.0–7.6 (m, 17H, aromatic H's+H5A+H5B); 8.00 (d, J=7.3 Hz, 4H, aromatic H's ortho to CONH); 8.12, 8.52 (two d, J=7.3 Hz, 2H, H6A+H6B); 11.20 (bs, 2H, 2 N$H$CO). $^{31}$P NMR (81 MHz, DMSO-$d_6$): δ=54.22 ($H_3PO_4$ as external reference).

FAB-MS: m/z 1201 ([M+Na]$^+$); as sodium salt.

The lower $R_f$ compound was the $S_P$ isomer (VIIb) (5.81 g, 42% yield). TLC on silica gel: $R_f$ 0.25 eluting with ethyl acetate/methanol 85:15.

$^1$H NMR (400 MHz, DMSO-$d_6$): δ=0.02 (s, 6H, 2 Si$CH_3$); 0.82 (s, 9H, SiC($CH_3$)$_3$); 2.0–2.7 (m, 4H, $CH_2$2'A+$CH_2$2'B); 3.2–3.5 (m, 2H, $CH_2$5'A); 3.67 (s, 6H, 2 $OCH_3$); 3.90 (m, 2H, $CH_2$5'B); 3.96 (m, 1H, H4'B); 4.28 (m, 1H, H4'A); 4.44 (m, 1H, H3'B); 5.04 (m, 1H, H3'A); 6 12, 6 16 (two dd, J=6.4 Hz, 2H, H1'A+H1'B); 6.83 (dd, J=aromatic H's ortho to $OCH_3$); 7.0–7.6 (m, 17H, aromatic H's+H5A+H5B); 7.94 (d, J=7.3 H's ortho to CONH); 8.12, 8.45 (two d, J=7.3 Hz, 2H, H6A+H6B); 11.20 (bs, 2H, 2 N$H$CO). $^{31}$P NMR (81 MHz, DMSO-$d_6$): δ=54.70 ($H_3PO_4$ as external reference).

FAB-MS: m/z 1201 ([M+Na]$^+$); as sodium salt.

Example 2

$N^4$-benzoyl-5'-O-(dimethoxytrityl)- 2'-deoxy-($R_P$)-P-thiocytidylyl-(3'→5')-$N^4$-benzoyl-2'-deoxycytidine, tetrabuthylammonium salt (VIIIa with $R^1$=DMT, $R^2$=Bz)

0.2M Tetrabutyl ammonium fluoride solution in tetrahydrofuran/pyridine 4:1 (40 ml, 8 mmol was added to $N^4$-benzoyl-5'-O-(dimethoxytrityl)-2'-deoxy-($R_P$)-p-thiocytidylyl-(3'→5')-$N^4$-benzoyl-3'-O-(t.butyldimethylsilyl)-2'-deoxycytidine, triethylammonium salt (VIIA) (4.05 g, 3.2 mmol) and the resulting solution was stirred overnight at room temperature. The reaction mixture was evaporated under reduced pressure, the residue was dissolved in methylene chloride and the organic solution washed with water. The purification was performed by silica gel column chromatography eluting with ethyl acetate/methanol 8:2 to give the title compound (VIIIa) as a white solid (3.28 g, 80% yield). $^1$H NMR (200 MHz, DMSO-$d_6$): δ=2.0–2.3 (m, 2H, $CH_2$2'B); 2.3–2.7 (m, 2H, $CH_2$2'A); 3.0–3.5 (m, 2H, $CH_2$5'A); 3.8–4.0 (m, 3H, H4'B+$CH_2$5'B); 4.30 (m, 2H, H3'B+H4'A); 5.02 (m, 1H, H3'A); 6.14, 6.16 (two dd, J=6.3 Hz, 2H, H1'+H1'B); 6.86 (d, J=8.8 Hz, 4H, aromatic H's ortho to $OCH_3$); 7.0–7.7 (m, 17H, aromatic H's+H5A+H5B); 7.97 (d, J=7.0 Hz, 4H, aromatic H's ortho to CONH); 8.09, 8.50 (two d, J=7.5 Hz, 2H, H6A+H6B).

FAB-MS (negative ions): m/z 1041 ([M-H]$^-$); as free acid.

Example 3

N4-benzoyl-5'-O-(dimethoxytrityl)-2'-deoxy- ($S_P$)-P-thiocytidylyl-(3'→5')-$N^4$-benzoyl-2'-deoxycytidine, tetrabuthylammonium salt (VIIIb with $R^1$=DMT, $R^2$=Bz)

$N^4$-benzoyl-5'-O-(dimethoxytrityl)-2'-deoxy-($S_P$)-P-thiocytidylyl-(3'→5')-$N^4$-benzoyl-3'-O-(t.butyldimethylsilyl)-2'-deoxycytidine, triethylammonium salt (VIIb) (4.15 g, 3.3 mmol) was treated as described in example 2 to give the title compound (VIIIb) (4.4g, 95% yield).

$^1$H NMR (200 MHz, DMSO-$d_6$): δ=1.9–2.3 (m, 2H, $CH_2$2'B); 2.3–2.6 (m, 2H, $CH_2$2'A); 3.0–3.4 (m, 2H, $CH_2$5'A); 3.69, 3.70 (two s, 6H, 2$OCH_3$); 3.90 (m, 2H, $CH_2$5'B); 3.96 (m, 1H, H4'B); 4.28 (m, 2H, H3'B+H4'A); 5.02 (m, 1H, H3'A); 6.13, 6.17 (two m, 2H, H1'A+H1'B); 6.85 (d, J=8.8 Hz, 4H, aromatic H's ortho to $OCH_3$); 7.0–7.7 (m, 17H, aromatic H's+H5A+H5B); 7.98 (d, J=7.1 Hz, 4H, aromatic H's ortho to CONH); 8.10, 8.47 (two d, J=7.3 Hz, 2H, H6A+H6B); 11.17, 11.23 (two bs, 2H, 2 N$H$CO).

FAB-MS: m/z 1087 ([M+Na]$^+$); 1065 ([M+H]$^+$); as sodium salt.

Example 4

$N^4$benzoyl-5'-dimethoxytrityl)-2'-deoxy-($R_P$)-P-thiocytidylyl-(3'→5')-$N^4$-benzoyl-3'-O-(hydrogenphosphonate)-2'-deoxycytidine, triethylammonium salt (IXa with $R^1$=DMT, $R^2$=Bz)

A stirred solution of fresh distilled phosphorus trichloride (1.1 ml, 12.5 mmol) and N-methyl morpholine (13.8 ml, 125 mmol) in dry methylene chloride (125 ml) was added, at room temperature, to 1,2,4-triazole (2.93 g, 42.5 mmol) dried under vacuum in the presence of phosphorus pentoxide.

After 30 minutes the reaction mixture was cooled to 0° C. and a solution of $N^4$-benzoyl-5'-O-(dimethoxytrityl)-2-deoxy-($R_P$)-P-thiocytidylyl-(3'5')-$N^4$-benzoyl-2'-deoxycytidine, tetrabuthylammonium salt (VIIIa) (3.2 g, 2.5 mmol) (dried by coevaporation with pyridine) in methylene chloride (40 ml) was added dropwise over 20 minutes. The reaction mixture was stirred for 10 minutes then poured into 1M aqueous triethylammonium hydrogen carbonate (100 ml), shaken and separated. The aqueous phase was extracted with methylene chloride (100×3 ml), then the combined organic phases were dried ($Na_2SO_4$) and evaporated to a foam. Purification by silica gel column chromatography eluting with methylene chloride/methanol/triethylammine 70:30:2, gave the title compound (IXa) (2,2 g, 67% yield) as a white foam.

$^1$H NMR (400 MHz, DMSO-$d_6$): i.a. δ=2.2–2.6 (m, 4H, $CH_2$2'A+$CH_2$2'B); 3.70 (s, 6H, 2 $OCH_3$); 3.9–4.4 (m, 4H, $CH_2$5'B+H4'A+H4'B); 4.90, 5.08 (two m, 2H, H3'A+H3'B); 6.65 (d, J=605 Hz, 1H, P-H); 6.18 (m, 2H, H1'A+H1'B); 6.87 (d, J=8.5 Hz, 4H, aromatic H's ortho to $OCH_3$); 7.0–7.6 (m, 17H, aromatic H's+H5A+H5B); 7.98 (m, 4H, aromatic H's ortho to CONH); 8.11, 8.60 (two m, 2H, H6A+H6B); 11.18, 11.24 (two bs, 2H, 2 N$\underline{H}$CO). FAB-MS (negative ions): m/z 1127 ([M+Na-2H]–); as free acid.

Example 5

N4 -benzoyl-5'-O-(dimethoxytrityl) -2'-deoxy-($S_P$)-P-thiocytidylyl-(3'→5')-$N^4$-benzoyl-3'-O-(hydrogenphosphonate)-2'-deoxycytidine, triethylammonium salt (IXb with $R^1$=DMT, $R^2$=Bz)

$N^4$benzoyl-5'-O-(dimethoxytrityl)-2'-deoxy-($S_P$)-P-thiocytidylyl-(3'→5')-$N^4$-benzoyl-2'-deoxycytidine tetrabuthylammonium salt (VIIIb) (3.85 g, 3 mmol) was treated analogously to what is described in example 4 to give the title compound (IXb) (2.16 g, 55% yield).

$^1$H NMR(400 MHz, DMSO-$d_6$): δ=2.1–2.7 (m, 4H, $CH_2$2'A+$CH_2$2'B); 3.2–3.4 (m, 2H, $CH_2$5'A); 3.71 (s, 6H, 2 $OCH_3$); 3.9–4.2 (m, 3H, $CH_2$5'B+H4'A); 4.38 (m, 1H, H4'A); 4.80, 5.10 (two m, 2H, H3'A+H3'B); 6.18 (m, 2H, H1'A+H1'B); 6.65 (d, J=605 Hz, 1H, P-H); 6.85 (d, J=8.5 Hz, 4H, aromatic H's ortho to $OCH_3$); 7.0–7.6 (m, 17H, aromatic H's+H5A+H5B); 8.00, 8.01 (two d, J=7.3 Hz, 4H, aromatic H's ortho to CONH); 8.07, 8.38 (two d, J=7.3 Hz, 2H, H6A+H6B); 11.09 (bs, 2H, 2 N$\underline{H}$CO).

Example 6

$N^4$benzoyl-2'-deoxy-($R_P$)-P-thiocytidylyl-(3'→5')-$N^4$-benzoyl-3'-O-(hydrogenphosphonate)-2'-deoxycytidine, triethylammonium salt (Xa with $R^2$=Bz)

Benzenesulphonic acid (1.53 g, 9.67 mmol) was added to a ice cooled solution of $N^4$benzoyl-5'-O-(dimethoxytrityl)-2'-deoxy-($R_P$)-P-thiocytidylyl-(3'→5')-$N^4$benzoyl-3'-O-(hydrogenphosphonate)-2'-deoxycytidine, triethylammonium salt (IXa) (2.0 g, 1.53 mmol) in methylene chloride/methanol 7:3 (76 ml).

The reaction mixture was stirred for 10 minutes, then was poured into 1.0 M aqueous triethylammonium hydrogen carbonate (100 ml). The organic phase was washed several times with water then the aqueous extracts were collected and concentrated under reduced pressure. The crude was purified by reverse-phase column chromatography on $R_P$ 8 using a linear gradient from 0% to 20% of acetonitrile in water to give the title compound (Xa) as a white lyophile (1.12 g, 73% yield).

$^1$H NMR (400 MHz, DMSO-$d_6$): δ=2.0–2.6 (m, 4H, $CH_2$2'A+$CH_2$2'B); 3.68 (m, 2H, $CH_2$5'A); 4.2–4.4 (m, 4H, H4'A+H4'B+$CH_2$5'B); 4.88 (m, 2H, H3'A+H3'B); 6.17 (m, 2H, H1'A+H1'B); 6.62 (d, J=605 Hz, 1H, P-H); 7.2–7.6 (m, 8H, aromatic H's+H5A+H5B); 7.98 (d, J=7.4 Hz, 4H, aromatic H's ortho to CONH); 8.40, 8.61 (two d, J=8.0 Hz, 2H, H6A+H6B); 11.20 (bs, 2H, 2 N$\underline{H}$CO).

FAB-MS: m/z 827 ([M+Na]$^+$); as free acid.

Example 7

$N^4$-benzoyl-2'-deoxy-($S_P$)-P-thiocytidylyl-(3'→5')-$N^4$-benzoyl-3'-O-(hydrogenphosphonate)-2'-deoxycytidine, triethylammonium salt (Xb with $R^2$=Bz)

$N^4$-benzoyl-5'-O-(dimethoxytrityl)-2'-deoxy-($S_P$)-P-thiocytidylyl-(3'→5')-$N^4$benzoyl-3'-O-(hydrogenphosphonate)-2'-deoxycytidine, triethylammonium salt (IXb) (2.19 g, 1.67 mmol) was treated analogously to what is described in example 6 to give the title compound (Xb) (1.01 g, 60% yield).

$^1$H NMR (400 MHz, DMSO-$d_6$): δ=2.1–2.7 (m, 4H, $CH_2$2'A+$CH_2$2'B); 3.66 (m, 2H, $CH_2$5'A); 4.0–4.3 (m, 4H, H4'A+H4'B+$CH_2$5'B); 4.94 (m, 1H, H3'B ); 5.01 (m, 1H, H3'A); 6.16, 6.20 (two m, 2H, H1'A+H1'B); 6.65 (d, J=600 Hz, 1H, P-H); 7.2–7.7 (m, 8H, aromatic H's+H5A+H5B); 7.98, 8.01 (two d, J=7.0 Hz, 4H, aromatic H's ortho to CONH); 8.33, 8.39 (two d, J=7.3 Hz, 2H, H6A+H6B); 11.15 (bs, 2H, 2 N$\underline{H}$CO).

FAB-MS: m/z 871 ([M+Na]$^{30}$); 849 ([M+H]$^+$); as sodium salt.

Example 8

Cyclo-$N^4$-benzoyl-2'-deoxy-($R_P$)-P-thiocytidylyl-(3'→5')$N^4$-benzoyl-2'-deoxy-($R_P$)-P-thiocytidylyl-(3'→5'), triethylammonium salt (XIa with R2=Bz)

$N^4$benzoyl-2'-deoxy-($R_P$)-P-thiocytidylyl-(3'→5')-$N^4$-benzoyl-3'-O-(hydrogenphosphonate) 2'-deoxycytidine, triethylammonium salt (Xa) (0.84 g, 8.34 mmol) was dried by coevaporation with pyridine, dissolved in pyridine (23 ml) and dimethylformamide (2 ml).

Pivaloyl chloride (0.3 ml, 2.5 mmol) was added dropwise and the reaction mixture was stirred at room temperature for 30 minutes under nitrogen atmosphere. Elemental sulphur (2.67 g, 83.4 mmol) was added, and after three hours the reaction was quenched by addition of diethylamine (5 ml).

The reaction mixture was concentrated under reduced pressure, the crude was washed with water and the sulphur excess filtered off.

The aqueous solution was purified by reverse phase column chromatography on $R_P$ 8 using water/acetonitrile 9:1. The fractions containing the product were combined and lyophilized to obtain the title compound (XIa) as a white solid (0.47 g, 55% yield).

$^1$H NMR (200 MHz, DMSO-$d_6$): δ=2.2–2.5 (m, 4H, $CH_2$2'A+$CH_2$2'B); 3.7–4.1 (m, 6H, H4'A+H4'B+$CH_2$5'A+$CH_2$5'B); 4.69 (m, 2H, H3'A+H3'B); 6.03 (m, 2H, H1'A+H1'B); 7.32 (d, J=7.5 Hz, 2H, H5A+H5B); 7.46 (m, 4H, aromatic H's meta to CONH); 7.55 (m, 2H, aromatic H's para to CONH); 7.94 (d, J=7.6 Hz, 4H, aromatic H's ortho to CONH); 8.39 (d, J=7.5 Hz, 2H, H6A+H6B); 11.17 (bs, 2H, 2 N$\underline{H}$CO).

FAB-MS: m/z 841 ([M+Na]$^{30}$); 819 ([M+H]$^+$); as free acid.

Example 9

Cyclo-$N^4$-benzoyl-2'-deoxy-($S_P$)-p-thiocytidylyl-(3'→5')$N^4$-benzoyl-2'-deoxy-($R_P$)-P-thiocytidylyl-(3'→5'), triethylammonium salt (XIb with $R^2$=Bz)

$N^4$-benzoyl-2'-deoxy-($S_P$)-p-thiocytidylyl-(3'→5')-$N^4$-benzoyl-3'-O-(hydrogenphosphonate)-2'-deoxycytidine, triethylammonium salt (Xb) (1.01 g, 1.0 mmol) was treated analogously to what is described in example 8 to give the title compound (XIb) (0.5 g, 49% yield).

$^1$H NMR (400 MHz, DMSO-$d_6$): δ=2.3–2.6 (m, 2H, $CH_2$2'A+$CH_2$2'B); 3.7–4.2 (m, 6H, H4'A+H4'B +$CH_2$5'A+$CH_2$5'B); 4.77 (m, 2H, H3'A+H3'B); 6.05 (m, 2H, H1'A+

H1'B); 7.29, 7.37 (two bs, 2H, H5A+H5B); 7.47 (m, 4H, aromatic H's meta to CONH); 7.58 (m, 2H, aromatic H's para to CONH); 7.98 (d, J=7.6 Hz, 4H, aromatic H's ortho to CONH); 8.40, 8.66 (two d, J=7.6 Hz, 2H, H6A+H6B); 10.96, 11.04 (two bs, 2H, 2 NHCO).

FAB-MS: m/z 841 ([M+Na]$^{30}$); as free acid.

Example 10

Cyclo-2'-deoxy-($R_P$)-P-thiocytidylyl-(3'→5')-2'-deoxy-($R_P$)-P-thiocytidylyl-(3'→5'), sodium salt (IIa)

Cyclo-$N^4$-benzoyl-2'-deoxy-($R_P$)-p-thiocytidylyl-(3'→5')-$N^4$-benzoyl-2'-deoxy-($R_P$)-P-thiocytidylyl-(3'→5'), triethylammonium salt (XIa) (0.33 g, 0.32 mmol) was dissolved in 17% aqueous ammonia solution (87 ml) and stirred in a sealed vessel for 3 hours at 50° C.

The reaction mixture was cooled to room temperature and concentrated under vacuum.

The reissues was dissolved in water and the insoluble benzoylamide was filtered off.

The filtrate was purified by reverse phase column chromatography on $R_P$ 8 eluting with water.

The fractions containing the product were lyophilized and the white solid so obtained was dissolved in water and passed through a Dowex 50W-X8 sodium strong cation exchanger column. The resulting aqueous solution was freeze-dried to give the title compound as sodium salt (IIa) (180 mg, 85% yield).

$^1$H NMR (400 MHz, DMSO-$d_6$): δ=2.0–2.4 (m, 4H, CH$_2$2'A+CH$_2$2'B); 3.6–4.0 (m, 6H, CH$_2$5'A+CH$_2$5'B+ H4'A+H4'B); 4.68 (m, 2H, H3'A+H3'B); 5.66 (d, J=7.5 Hz, 2H, H5A+H5B); 5.99 (m, 2H, H1'A+H1'B); 7.02, 7.16 (two bs, 4H, 2 NH$_2$); 7.82 (d, J=7.5 Hz, 2H, H6A+H6B).

$^{31}$P NMR (81 MHz, DMSO-$d_6$): δ=53.03 (H$_3$PO$_4$ as external reference).

FAB-MS: m/z 655 ([M+H]$^+$); as sodium salt.

Example 11

Cyclo-2'-deoxy-($S_P$)-P-thiocytidylyl-(3'→5')-2'-deoxy-($R_P$)-P-thiocytidylyl-(3'→5'), sodium salt (IIb)

Cyclo-$N^4$-benzoyl-2'-deoxy-($S_P$)-P-thiocytidylyl-(3'→5')-$N^4$-benzoyl-2'-deoxy-($R_P$)-P-thiocytidylyl-(3'→5'), triethylammonium salt (XIb) (0.5 g, 0.49 mmol) was treated analogously to what is described in example 10 to give the title compound (IIb) (0.23g, 72% yield).

$^1$H NMR (400 MHz, DMSO-$d_6$): δ=2.0–2.4 (m, 4H, CH$_2$2'A+CH$_2$2'); 3.6–4.0 (m, 6H, CH$_2$5'A+CH$_2$5'B +H4'A+ H4'B); 4.68 (m, 2H, H3'A+H3'B); 5.64, 5.73 (two m, J=7.5 Hz, 2H, H5A+H5B); 5.99 (two m, 2H, H1'A+H1'B); 6.92, 7.00, 7.11, 7.15 (four bs, 4H, 2 NH$_2$); 7.78, 8.10 (two d, J=7.5 Hz, 2H, H6A+H6B).

$^{31}$p NMR (81 MHz, DMSO-$d_6$): δ=53.19, 52.94 (H$_3$PO$_4$ as external reference).

FAB-MS: m/z 677 ([M+Na]$^+$); 655 ([M+H]$^+$); as sodium salt.

Example 12

2'-deoxy-($R_P$)-P-thiocytidylyl-(3'→5')-2'-deoxycytidine sodium salt (XIIa)

0.2M Tetrabutylammonium fluoride solution in tetrahydrofuran/pyridine 4:1 (3.125 ml) was added to $N^4$-benzoyl-5'-O-(dimethoxytrityl)-2'-deoxy-($R_P$)-P-thiocytidylyl-(3'→5')-$N^4$-benzoyl-3,-O-(t.butyldimethylsilyl)-2'-deoxycytidine triethylammonium salt (VIIa) (310 mg, 0.25 mmol) and the resulting solution was treated as described in example 2 to give a crude (VIIIa) that was used for the successive step.

The residue VIIIa was dissolved in dioxane (29 ml) and 30% aqueous ammonia solution was added (39 ml). The reaction mixture that was treated as in example 10. Benzenesulfonic acid (0.25 g) was added to a ice cooled solution of the above obtained crude in methylenechloride/methanol 7:3 (12.5 ml). The reaction mixture was stirred for 10 minutes than was poured into 1.0M aqueous triethylammonium hydrogen carbonate (20 ml). The aqueous layer was washed with diethylether and concentrated under reduced pressure.

The crude was purified by reverse phase column chromatography on $R_P$ 8 eluting with water. The fractions containing the product were lyophilized and the white solid so obtained was dissolved in water and passed through a Dowex 50W-X8 sodium strong cation exchanger column.

The resulting aqueous solution was freeze-dried to give the title compound as sodium salt (XIIa) (80 mg, 58% overall yield).

$^1$H NMR (200 MHz, DMSO-$d_6$): δ=1.8–2.3 (m, 4H, CH$_2$2'A+CH$_2$2'); 3.57 (m, 2H, CH$_2$5'A); 3.8–3.9 (m, 3H, CH$_2$5'B+H4'B); 4.01 (m, 1H, H4'A); 4.25 (m, 1H, H3'B); 4.76 (m, 1H, H3'A); 5.71 (d, J=7.5 Hz, 2H, H5A+H5B); 6.17 (m, 2H, H1'A+H1'B); 7.0–7.2 (bs, 4H, 2 NH$_2$); 7.79, 7.92 (two d, J=7.5 Hz, 2H, H6A+H6B).

$^{31}$P NMR (81 MHz, DMSO-$d_6$): δ=54.27 (H$_3$PO$_4$ as external reference).

FAB-MS: m/z 555 ([M+H]$^+$)

Example 13

2'-deoxy-($S_P$)-P-thiocytidylyl-(3'→5'-2-deoxycytidine sodium salt (XIIb)

$N^4$-benzoyl-5'-O-(dimethoxytrityl)-2'-deoxy-($S_P$)-P-thiocytidylyl-(3'→5')-$N^4$-benzoyl-3'-O-(t.butyldimethylsilyl)-2'-deoxycytidine, triethylammonium salt (VIIb) (400 mg, 0.32 mmol) was treated analogously to what is described in example 12 to give the title compound (XIIb) (100 mg, 55% overall yield).

$^1$H NMR (400 MHz, DMSO-$d_6$): δ=1.8–2.0 (m, 2H, CH(H)2'A+CH(H)2'B); 2.01 (m, 1H, CH(H)2'B); 2.25 (m, 1H. CH(H)2'A); 3.53 (m, 2H, CH$_2$5'A); 3.7–3.9 (m, 3H, CH$_2$5'B+H4'B); 3.95 (m, 1H, H4'A); 4.21 (m, 1H, H3'B); 4.73 (m, 1H, H3'A); 5.69, 5.70 (two d, J=7.2 Hz, 2H, H5A+H5B); 6.11 (m, 1H, H'A); 6.17 (m, 1H, H1'B); 6.9–7.1 (bs, 4H, 2 NH$_2$); 7.75, 7.89 (two d, J=7.2 Hz, 2H, H6A+H6B).

$^{31 P NMR}$ (81 MHz, DMSO-$d_6$): δ=54.45 (H$_3$PO$_4$ as external reference).

FAB-MS: m/z 577 ([M+Na]$^{30}$); 555 ([M+H]$^+$).

Example 14

Enzymatic hydrolysis of the deprotected dinucleotide thiophosphates

The relative susceptivity of the two substrates XIIa and XIIb to hydrolysis by snake venom phosphodiesterase was determined by incubating a solution (3 mM) of each substrate in Tris buffer (25 mM) containing MgCl$_2$ (5 mM) at pH 8 with the enzyme (1 mg in 0.5 ml) (from *Crotalus durissus*) purchased from Boehringer and following the substrate disappearance by HPLC. In particular for each substrate a solution was prepared consisting of 700 μl of buffer, 200 μl of substrate solution plus 50 μl of enzyme solution. For each substrate a control was prepared with the same components and volumes except for the enzyme that was replaced by an equal volume of buffer. The four solutions (the two substrates and the two controls) were incubated at 37° C. taking aliquots from each solution at 0 time, 1 hour, 17 hours. Such aliquots were analyzed by HPLC (Whatman Partisphere C18, eluting with a linear gradient from 10% to 30% of methanol 0.1 M ammonium acetate) at 220 nm.

Only XIIa a showed a marked reduction in the area of the HPLC peak relatively to the control: 50% after 1 hour and 72% after 17 hours. This indicates the $R_P$ configuration for XIIa.

In the other case the dinucleotide XIIb remained almost unchanged both after 1 hour and after 17 hours indicating the $S_p$ configuration for the substrate.

Example 15

Tablets each weighing 0.250 g and containing 50 mg of the active substance, can be manufactured as follows:

Composition (for 10,000 tablets)

| | |
|---|---|
| Cyclo-2'-deoxy-($S_p$)-P-thiocytidylyl-(3'→5')-2'-deoxy ($R_p$)-P-thiocytidylyl-(3'→5'), sodium salt | 500 g |
| Lactose | 1400 g |
| Corn starch | 500 g |
| Talc powder | 80 g |
| Magnesium stearate | 20 g |

The cyclo-2'-deoxy-($S_P$)-P-thiocytidylyl-(3'→5')-2'-deoxy-($R_P$)-P-thiocytidylyl-(3'→5') sodium salt the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium is added, carefully mixed and processed into tablets.

Example 16

Capsules, each dosed at 0.200 g and containing 20 mg of the active substance can be prepared as follows:

Composition for 500 capsules:

| | |
|---|---|
| Cyclo-2'-deoxy-($S_p$)-P-thiocytidylyl-(3'→5')-2'-deoxy ($R_p$)-P-thiocytidylyl-(3'→5'), sodium salt | 10 g |
| Lactose | 80 g |
| Corn starch | 5 g |
| Magnesium stearate | 5 g |

This formulation can be encapsulated in two-piece hard gelatin capsules and dosed at. 0.200 g for each capsule.

Example 17

Intravenous injection 25 mg/ml

An injectable pharmaceutical composition can be manufactured by dissolving 25 g of Cyclo-2'-deoxy-($S_P$)-P-thiocytidylyl-(3'→5')-2'-deoxy-($R_P$)-P-thiocytidylyl-(3'→b 5') sodium salt in sterile aqueous saline solution for injection (1000 ml) and sealing ampoules of 1–5 ml,

We claim:

1. A compound of formula (I)

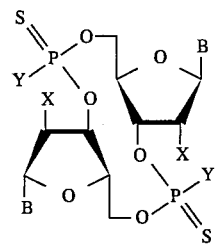

wherein
- each group B is, independently, a naturally occurring or modified heterocyclic base linked through a nitrogen or a carbon atom of the ring to the sugar moiety;
- each group X is, independently, hydrogen, fluorine, or hydroxy;
- each group Y is, independently, hydrogen, sulphidryl or hydroxy; and
- the pharmaceutically acceptable salts thereof.

2. A compound of formula (I) according to claim 1 wherein
- each group B is, independently, cytosine, thymine, uracil, guanine, adenine or hypoxanthine;
- X is hydrogen;
- Y is hydroxy; and
- the pharmaceutically acceptable salts thereof.

3. A compound of formula (I) according to claim 1, which is:
- cyclo-2'-deoxy-P-thiocytidylyl-(3'→5')-2'-deoxy-P-thiocytidylyl-(3'→5') or
- cyclo-2'-deoxy-P-thio-thiothymidylyl-(3'→5')-2'-deoxy-P-thiothymidylyl-(3'→5') in the form of $R_PR_P$ or $S_PR_P$ diastereomer or diastereomeric mixture, and the pharmaceutically acceptable salts thereof.

4. A compound of formula (I)

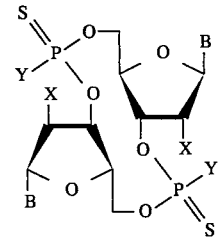

wherein
- each group B is a cytosine residue linked through the nitrogen at the 1-position of the ring to the sugar moiety;
- each group X is hydrogen; and
- each group Y is hydroxy; or a pharmaceutically acceptable salt thereof.

5. A compound of the formula (I) according to claim 4, which is cyclo-2'-deoxy-P-thiocytidylyl-(3'→5')-2'-deoxy-P-thiocytidylyl-(3'→5') in the form of $R_PR_P$ or $S_PR_P$ diastereomer or diastereomeric mixture, or a pharmaceutically acceptable salt thereof.

6. A pharmaceutical composition comprising a suitable carrier and, as an active principle, a compound of formula (I) as defined in claim 4 or a pharmaceutically acceptable salt thereof.

* * * * *